United States Patent
Ineichen

(10) Patent No.: US 11,033,435 B2
(45) Date of Patent: Jun. 15, 2021

(54) MULTIFUNCTIONAL WOUND TREATMENT DRESSING

(71) Applicant: Carag AG, Baar (CH)

(72) Inventor: Markus Ineichen, Kusnacht (CH)

(73) Assignee: CARAG AG, Baar (CH)

( * ) Notice: Subject to any disclaimer, the term of this patent is extended or adjusted under 35 U.S.C. 154(b) by 483 days.

(21) Appl. No.: 15/744,977

(22) PCT Filed: Jul. 6, 2016

(86) PCT No.: PCT/EP2016/065947
§ 371 (c)(1),
(2) Date: Jan. 15, 2018

(87) PCT Pub. No.: WO2017/009130
PCT Pub. Date: Jan. 19, 2017

(65) Prior Publication Data
US 2018/0116877 A1    May 3, 2018

(30) Foreign Application Priority Data

Jul. 16, 2015    (EP) ..................... 15177153

(51) Int. Cl.
*A61F 13/00* (2006.01)
*A61F 13/02* (2006.01)
*A61N 1/36* (2006.01)

(52) U.S. Cl.
CPC .. *A61F 13/00068* (2013.01); *A61F 13/00063* (2013.01); *A61F 13/0233* (2013.01); *A61F 2013/0028* (2013.01); *A61N 1/36014* (2013.01)

(58) Field of Classification Search
CPC .......... A61F 13/00068; A61F 13/00063; A61F 13/0233; A61F 13/00085;
(Continued)

(56) References Cited

U.S. PATENT DOCUMENTS 7,211,060 B1 * 5/2007 Talish ................... A61N 7/00
                                                                600/407
8,447,375 B2 * 5/2013 Shuler ................ A61B 5/14539
                                                                600/344
(Continued)

FOREIGN PATENT DOCUMENTS

WO    2006/114638 A2    11/2006
WO    2007/030599 A2    3/2007
(Continued)

OTHER PUBLICATIONS

International Search Report for PCT/EP2016/065947 dated Oct. 20, 2016.

*Primary Examiner* — Susan S Su
(74) *Attorney, Agent, or Firm* — Pearne & Gordon LLP

(57) ABSTRACT

A multifunctional wound treatment dressing for administering different therapeutic treatments to an open, chronic wound of a human or animal body. The multifunctional wound treatment dressing includes an occlusive wrapping adapted for placing over a wound. The multifunctional wound treatment dressing further includes at least two of the group of electrical, optical or mechanical stimulation means adapted for transmitting electrical, optical or mechanical energy towards the wound to stimulate healing of the wound and/or means for applying a negative (i.e. sub-atmospheric) pressure to the wound. Thus, a variety of different healing stimulation treatments may be performed together or in sequence by wearing the same occlusive wrapping without the need of changing/removing temporarily the wrapping for each change of treatment method.

20 Claims, 6 Drawing Sheets

(58) Field of Classification Search
CPC ........ A61F 2013/0028; A61F 2013/002; A61F 15/01; A61N 1/18; A61N 1/36; A61N 1/36014; A61N 1/36031; A61N 1/36034
See application file for complete search history.

(56) References Cited

U.S. PATENT DOCUMENTS

| | | | | |
|---|---|---|---|---|
| 2001/0043943 | A1* | 11/2001 | Coffey | A61L 15/225 424/447 |
| 2005/0222544 | A1* | 10/2005 | Weston | A61F 13/00068 604/313 |
| 2009/0177051 | A1 | 7/2009 | Arons | |
| 2010/0204752 | A1* | 8/2010 | Tremblay | A61M 1/0023 607/50 |
| 2012/0109083 | A1* | 5/2012 | Coulthard | A61M 1/0066 604/319 |
| 2012/0259266 | A1* | 10/2012 | Quisenberry | A61F 13/00068 604/20 |
| 2013/0150923 | A1* | 6/2013 | Schnetz | A61H 39/002 607/59 |

FOREIGN PATENT DOCUMENTS

| | | | | |
|---|---|---|---|---|
| WO | WO-2007030599 | A2 * | 3/2007 | ............ A61M 27/00 |
| WO | 2010/093753 | A1 | 8/2010 | |
| WO | 2014/188070 | A1 | 11/2014 | |

\* cited by examiner

MULTIFUNCTIONAL WOUND TREATMENT DRESSING

TECHNICAL FIELD

The present invention pertains to a means for treating open, chronic wounds. More specifically the present invention relates to a wound treatment dressing for administering therapeutic treatment to an open, chronic wound of a human or animal body.

BACKGROUND OF THE INVENTION

Wound healing is impaired in some individuals, such as patients suffering from certain disorders. This impairment in wound healing often leads to chronic wounds, the ongoing treatment of which represents a significant medical burden. Traditional approaches to the care and management of chronic non-healing wounds include passive techniques such as applying antibiotics and protective wound dressings, e.g. comprising an agent such as silver to protect the wound against viral or bacterial penetration, relieving the wound of mechanical stresses, or the use of various techniques to remove wound exudate and necrotic tissue. For the most part, these treatment approaches do not lead to a lasting recovery but merely prevent a further exacerbation and at best provide temporary relief.

Therefore, active approaches are employed to decrease the healing time and increase the healing success of chronic non-healing wounds. These active approaches are especially directed to appropriately altering the wound environment in order to enhance healing conditions. Such alterations may include the application of negative pressure, e.g. applying a sub-atmospheric pressure or a vacuum to the wound, using a sealing dressing and a vacuum pump. Negative pressure draws fluid out of a wound, which inhibits bacterial growth, and furthermore draws blood into the wound. Both of these effects promote healing. It has also been shown that specific types of electrical stimulation will alter the wound environment in a positive way so that a normal wound healing process can occur and in some cases be accelerated. Electrical stimulation for instance leads to increased tissue oxygen levels as well as blood flow at the application area and prevents the swelling of tissue adjacent to the wound. Moreover, phototherapy (i.e. light therapy or heliotherapy) is commonly applied as anti-bactericidal treatment, wound healing treatment, anti-fungal treatment, anti-parasitic treatment, anti-viral treatment, skin condition treatment, as well as to minimize scarring. However, at present there still exists a need for effective and efficient wound treatment dressings that provide an increased healing rate for a broad range of different poorly healing, i.e. chronic, open wounds.

SUMMARY OF THE INVENTION

It is therefore an object of the present invention to provide an improved wound treatment dressing capable of effectively and flexibly administering an appropriate therapeutic treatment to a wide variety of open, chronic wounds of a human or animal body.

This object is achieved by the multifunctional wound treatment dressing according to claim 1. Specific embodiments of the proposed wound treatment dressing are provided in the dependent claims 2 to 14.

The present invention provides a multifunctional wound treatment dressing, comprising:

an occlusive wrapping adapted for placing over a wound on the surface of a skin, one side of the wrapping intended to face the wound and comprising a connector to be connected with an external apparatus box, further comprising a combination of at least two of the following means:

- a negative pressure means, forming a substantially fluid-tight seal around the wound; and/or
- an electrical stimulation means, comprising at least one electrode arranged at the wound treatment dressing and adapted for transmitting electrical energy towards the wound and/or
- an optical stimulation means, comprising an optical energy conducting and/or emitting element arranged at the wrapping and adapted for transmitting optical energy towards the wound; and/or
- a mechanical stimulation means, comprising a vibrational energy source, such as an ultrasound transducer, arranged at the wrapping and adapted for transmitting vibrational energy towards the wound; and/or
- means for removing wound exudates to an exterior of the wrapping.

Providing a plurality of therapeutic means within a single wound treatment dressing allows to appropriately select and rapidly employ whichever therapy or combination of therapies is most effective to treat and heal the specific open, chronic wound present. It especially allows to continuously apply a variety of different treatments or therapies to the wound without having to change the wound treatment dressing, which is typically a very tedious process as well as often being painful for the patient.

In a further embodiment of the wound treatment dressing the wrapping is flexible or is rigid or is partly flexible and partly rigid.

In a further embodiment of the wound treatment dressing the wrapping is individually customized according to the specific shape of a body part of an individual, at which body part the wound is located. Thus, some specific shapes may be provided for special body regions with specific contours, e.g. more flat regions or more curved regions of the body. A specific range of different sizes may be provided too, to cover smaller or bigger wounds to be treated. The wrapping may as an example be obtained by means of a three-dimensional (3D) printing or additive manufacturing process, in which successive layers of material are laid down under computer control.

In a further embodiment the wound treatment dressing further comprises a sensor for determining a state or status of the wound, for instance for monitoring a variety of parameters such as pH, temperature, tissue closure, infection, biomarkers of healing, enzymes or moisture level. By measuring or determining such parameters, the stimulation process may be altered during the treatment period to shorten the treatment time or to perform better results.

In a further embodiment of the wound treatment dressing the sensor comprises an optical sensor adapted for illuminating the wound and collecting information regarding the wound scattering parameters. For example, by observing the light reflection of the wound, the absorption rate of the wound or the skin may be derived for obtaining conclusions regarding the progress of the healing process of the wound.

In a further embodiment the wound treatment dressing further comprises means for analyzing fluid exudate removed from the wound via the port, in particular for identifying progress of wound healing. In particular, the means for analyzing the fluid exudate is adapted for determining one or more analytes indicative of one or more biochemical reactions that occur during wound recovery.

In a further embodiment the wound treatment dressing further comprises a control unit adapted for adjusting a parameter in the wound treatment dressing and/or at the wound site, in particular dependent on data provided by the sensor.

In a further embodiment of the wound treatment dressing the electrical stimulation means is adapted for providing pulsed electrical stimulation, in particular is capable of delivering electrical pulses at a pre-selected or controllable pulse rate and intensity. In particular, the electrical stimulation means is adjustable in response to changes in the determined state or status of the wound.

In a further embodiment of the wound treatment dressing the electrical stimulation means comprises an array of electrodes, in particular the electrical stimulation means is adapted for creating at least one composite electrode from at least one of the electrodes in the array. In particular, the electrode composition of the at least one composite electrode is adjustable in response to changes in the determined state or status of the wound. Thus, a very selective and specific wound treatment may be realized.

In a further embodiment of the wound treatment dressing the optical stimulation means is adapted to provide at least one of an infrared (IR), near-infrared (NIR), ultraviolet (UV, in particular UVB) emission towards the wound. The infrared emission especially being intended to influence a temperature at the wound.

In a further embodiment of the wound treatment dressing the optical stimulation means is adapted for providing pulsed optical stimulation, in particular is capable of delivering optical pulses at a pre-selected or controllable pulse rate and intensity. In particular, the optical energy conducting and/or emitting element is adapted for providing a selected light having substantially similar intensity across the wound site.

In a further embodiment, the optical energy emitting element comprises a plurality of emitting sources arranged at spaced locations along at least a portion of a periphery of the wound site.

In a further embodiment of the wound treatment dressing the optical energy conducting and/or emitting element comprises a light conducting substrate and at least one emitter mounted to emit light into the substrate. In particular, the optical energy emitting element comprises at least one light emitting diode (LED). Furthermore, the optical energy transmitting element may comprise at least one optical fiber, the optical fiber for instance being split at one end to form a plurality of sub-fibers.

In a further embodiment the wound treatment dressing comprises an external apparatus box and a connection arrangement, the connection arrangement being adapted to receive one or more optical fibers and/or cables and/or wires and/or suction tubes and being further adapted for providing a connection to at least two of the following:
 a pumping means for generating a sub-atmospheric pressure, e.g. a vacuum pump;
 an electrical power source;
 an optical source, such as an IR, NIR, UV (in particular UVB) source;
 a control unit.

In this way a single arrangement can be employed to connect the wound treatment dressing with (a variety of different) external equipment such as a vacuum source for negative pressure therapy, an electrical power source for electrical stimulation therapy or a light source for photo-therapy. Moreover, the same arrangement can be utilized to transfer measurement data obtained at the wound site from the wound treatment dressing to an external therapy monitoring and control device.

DETAILED DESCRIPTION OF THE INVENTION

Figure 1:
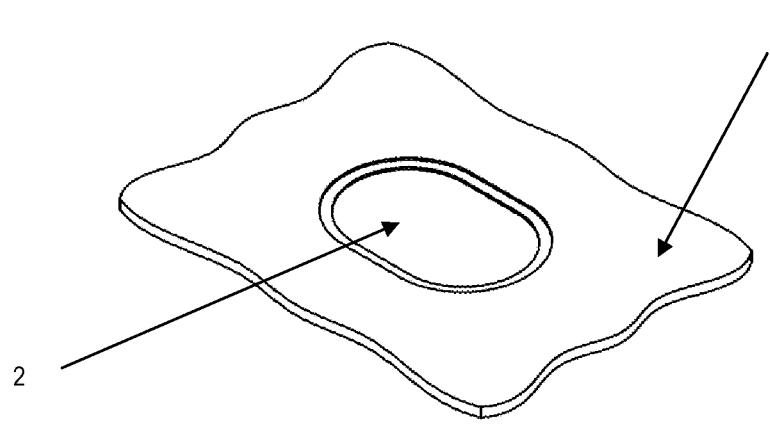
FIG. 1 is a perspective view to a wound area on a skin, drafted in a pure schematic manner.

FIG. 1 shows in a pure schematic manner the view onto a wound area 2 on a skin 1. The wound may be an excavation or an open cut in the skin of a person.

Figure 2:
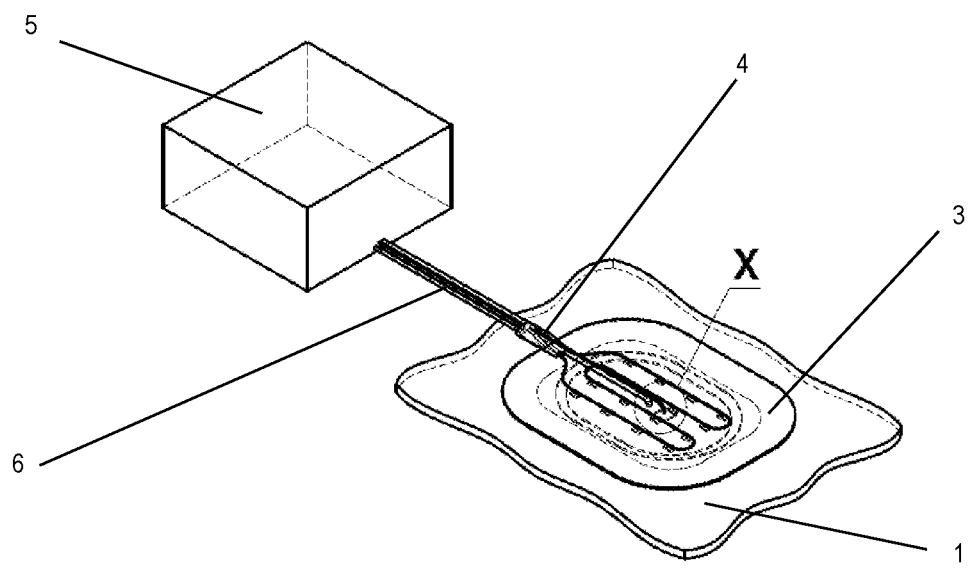
FIG. 2 is a perspective view of the wound treatment dressing according to the present invention applied to the wound area of FIG. 1.

FIG. 2 shows the upper view onto a wound treatment dressing that is applied onto the wound area 2 onto skin 1. An occlusive wrapping 3 is arranged over the area of the wound. This wrapping 3 is incorporating at least two or more stimulation means according to the present invention and build up a sealed environment around the wound.

Thus, a modular wound treatment dressing is provided composed of a basic wrapping 3 and an external apparatus box 5. The same external apparatus box 5 may be used for different types of wrappings 3, e.g. wrapping of different shape for different locations of the wound such as arms, elbows, knees or other peripheral locations and vice versa.

A pipe or tube 6 originating from the external apparatus box 5 is preferably detachable connected via a connector 4 to the wrapping 3, as shown in FIG. 2.

Preferably, the connector 4 is configured to have a plug-socket for detachably receiving the pipe 6 of the external apparatus box 5. Thus, the wrapping 3 can be placed at the appropriate location on the body with the wound to be treated without being disturbed by the pipe 6.

The external apparatus box 5 contains at least two of the following devices:
 a pumping means for generating a sub-atmospheric pressure, e.g. a vacuum pump;
 an electrical power source;
 an optical source, such as an IR, NIR, UV (in particular UVB) source;
 a control unit.

A suction tube 13 originating from pumping means (not shown) within the apparatus box 5 leads through the pipe 6 and the connector 4 into the occlusive wrapping 3. The end of this tube 8 protrudes into the area of the lower surface of the wrapping 3, thereby facing the wound 2 to be treated by the wound treatment dressing. By applying a sub-atmospheric pressure, the occlusive wrapping 3 is creating a sub-atmospheric pressure or a vacuum around the wound 2. The occlusive wrapping 3 is at the same time hold tight against the skin 1 around the wound 2, shielding the wound 2 to the outer atmosphere and protecting the wound area from outside influences.

In the example of FIG. 2, the wrapping 3 comprises furthermore the treatment part of an electrical stimulation means. An electrical wire 10 is arranged meandering within the wrapping 3 and has multiple junctions 11 arranged along its course to connect a treatment element 12 arranged in the lower surface of wrapping 3. The wire 10 is for example connected to an electrical source arranged within the apparatus box 5 for transmitting electrical energy to the wound 2. In this example, multiple treatment elements 12 are arranged in a serial manner with respect to the electrical source.

Figure 3:
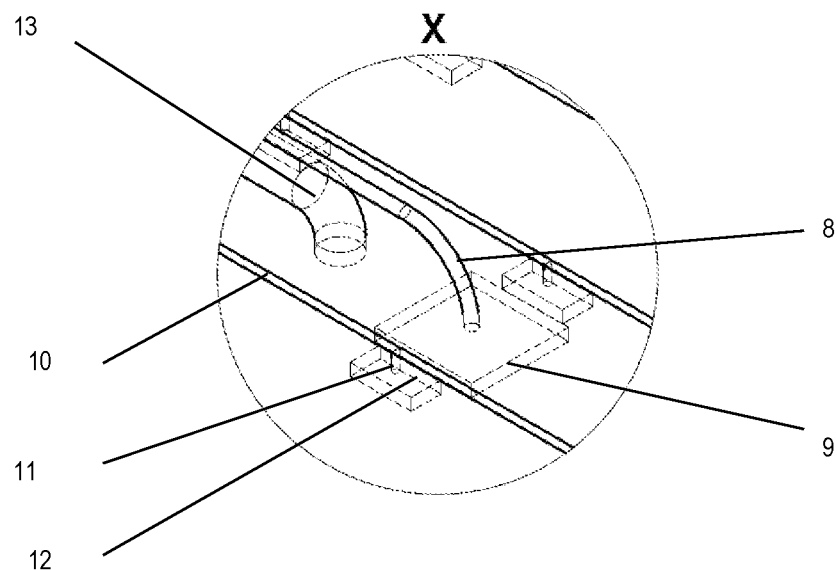
FIG. 3 is a detail perspective view into the central area of the occlusive wrapping of FIG. 2.

Details of the arrangement of these components are more clearly shown in the detail view of section X in FIG. 3.

A pressure sensor 9 is arranged at the lower surface of wrapping 3 to be close to the area of wound 2 and is connected via a cable 8 with a control unit arranged within the apparatus box 5. This sensor 9 provides data for adjusting the parameters of the wound treatment controlled by a control unit within the apparatus box 5 that controls the action of the electrical source for transmitting appropriate electrical energy to the wound 2 adopted to the ongoing healing process.

Preferably, one or more such sensors 9 can be arranged within wrapping 3 for determining the state or status of the wound 2, being connected to a respective analysis means arranged within the apparatus box 5. The sensors 5 may be adapted to monitor parameters such as pH, temperature, tissue closure, infection rate, biomarkers of healing, enzymes or moisture level.

It is even possible to combine multiple sensors of different types to measure or determine different parameters that can be used for determining the state of the wound healing process.

For the purpose of removing wound exudates, an additional suction tube may be arranged as well with its end protruding into the lower surface of wrapping 3 (not shown). The exudates may be collected in a receptacle (not shown) arranged exchangeable within the apparatus box 5 for immediate or later analyzing purpose.

The control unit may be configured to power and control the different means arranged within the apparatus box 5. The control unit may be configured to simply switch on and off the different means or to control the behavior of those means in a predetermined or adjustable manner.

Figure 4:
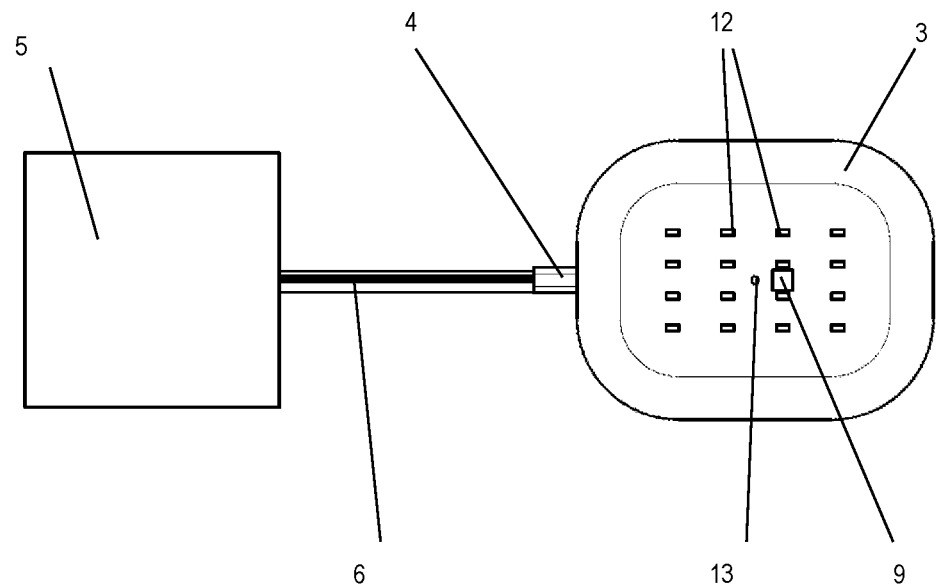
FIG. 4 is the bottom view onto the wound treatment dressing according to FIG. 2.

FIG. 4 shows the bottom-view onto the wound-facing side of the wound treatment dressing, depicting the treatment elements 12, the opening of the suction tube 13 and one sensor 9 in the area of wrapping 3 facing the wound 2.

Figure 5:
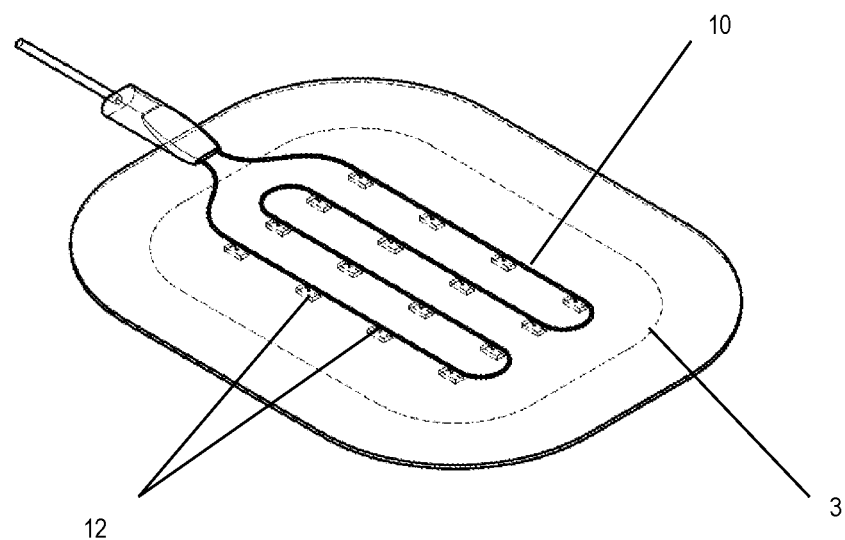
FIG. 5 is a perspective view of an embodiment with electrical stimulation means.

An alternative arrangement for a more individual control of the treatment elements 12 in shown in FIG. 5. In this example, multiple electrical wires 15 are connected individually to each treatment element 12 at the lower surface of wrapping 3. Those treatment elements 12 may thus transmit individual and/or different electrical energy emerging from an electrical stimulation means arranged within the apparatus box 5 to the wound 2. The treatment elements 12 may be of the same type or even of different types, according to the needs of the wound treatment process.

Figure 6:
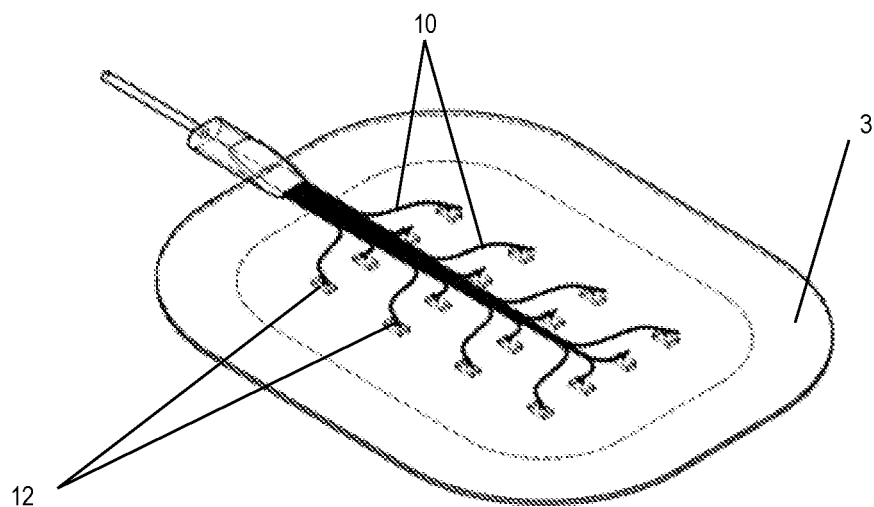
FIG. 6 is a perspective view of an alternative embodiment with electrical stimulation means.

FIG. 6 shows in even more details a section through a part of the wrapping 3. The specific treatment element 12, arranged at the lower side of the wrapping 3, is connected with its related individual wire 10, by a junction 11 that leads from the upper surface, where the wires 10 are arranged, through the wall of the wrapping 3 into the respective treatment element 12.

Figure 7:
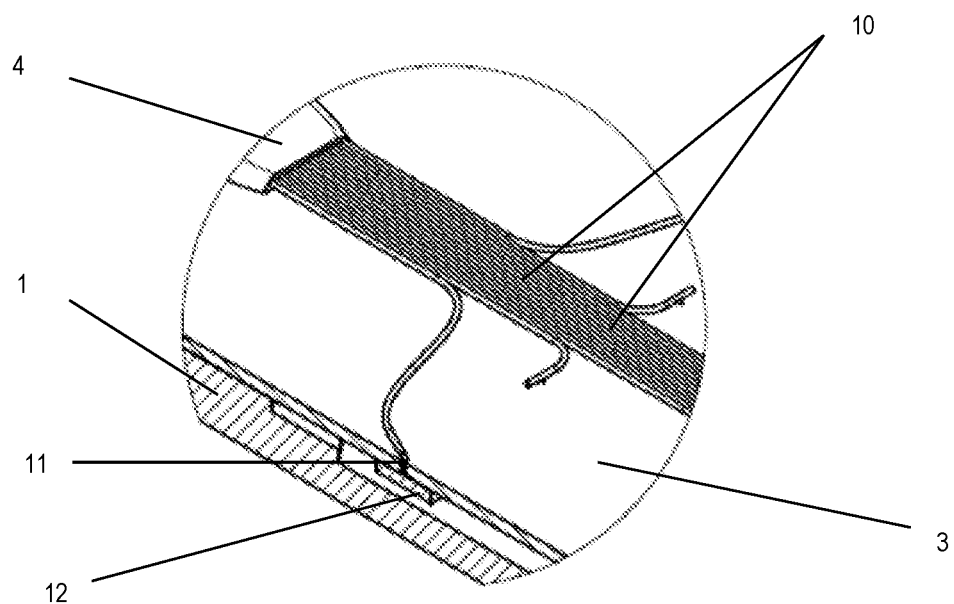
FIG. 7 is a detail sectional view of a part of the occlusive wrapping of FIG. 6.
Figure 8:
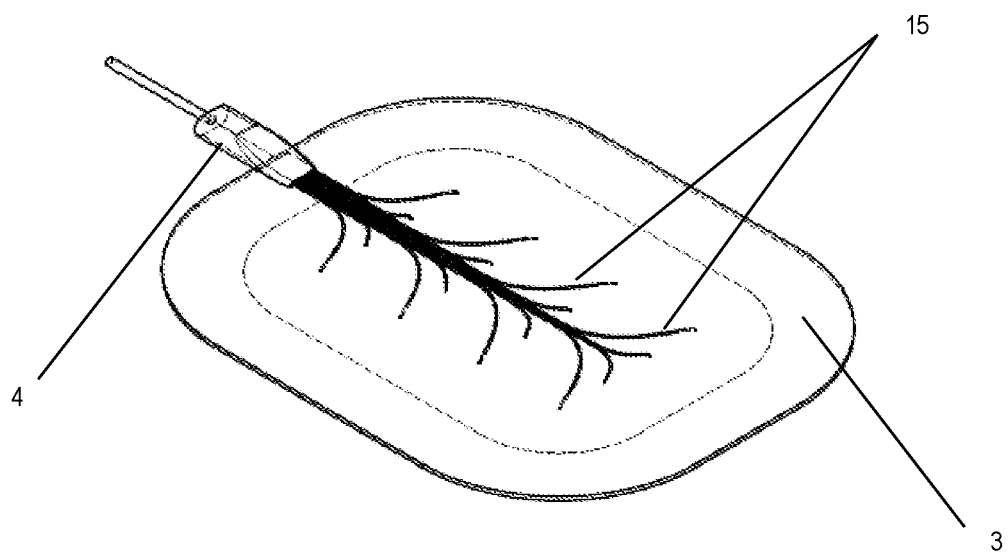
FIG. 8 is a perspective view of an embodiment for light treatment.
Figure 9:
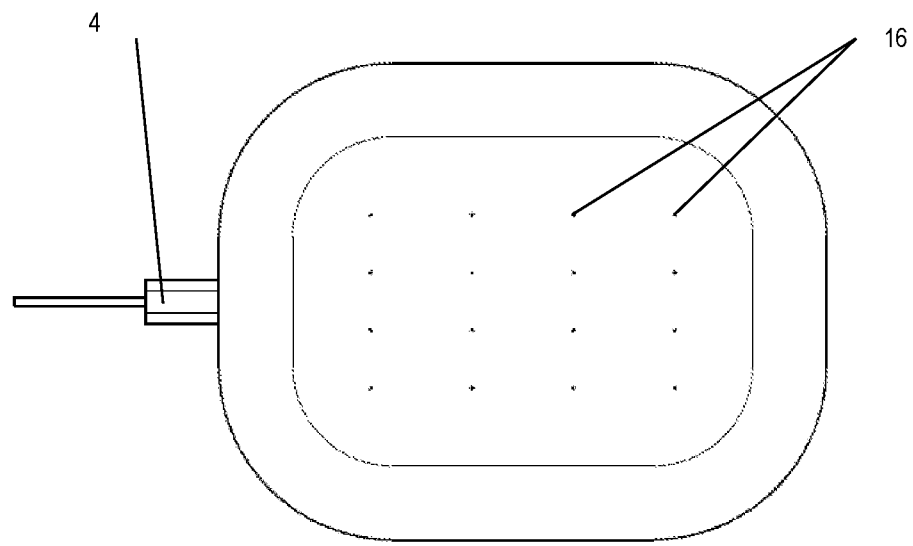
FIG. 9 is the bottom view of the embodiment of FIG. 8.

FIG. 7 refers to an example with optical stimulation means for wound treatment, having multiple optical fibers 15 arranged at the upper side of the wrapping 3. FIG. 8 shows the lower side of wrapping 3 with each fiber 15 leading into in a head 16 arranged at the lower side of wrapping 3 and directed to the wound 2. The heads 16 are emitting light directly through its opening onto the wound 2. Each of those light fibers 15 may be actuated individually, thereby enabling a localized light treatment of the wound, or may origin from one light fiber that is split into several sub-light fibers.

The light emitting source is located in an optical treatment stimulation means arranged in the apparatus box 5.

It is clear to the man skilled in the art that the light emitting means could be composed of light emitting diodes being arranged in the heads 16 and that are electrically connected to the apparatus box 5.

Figure 10:
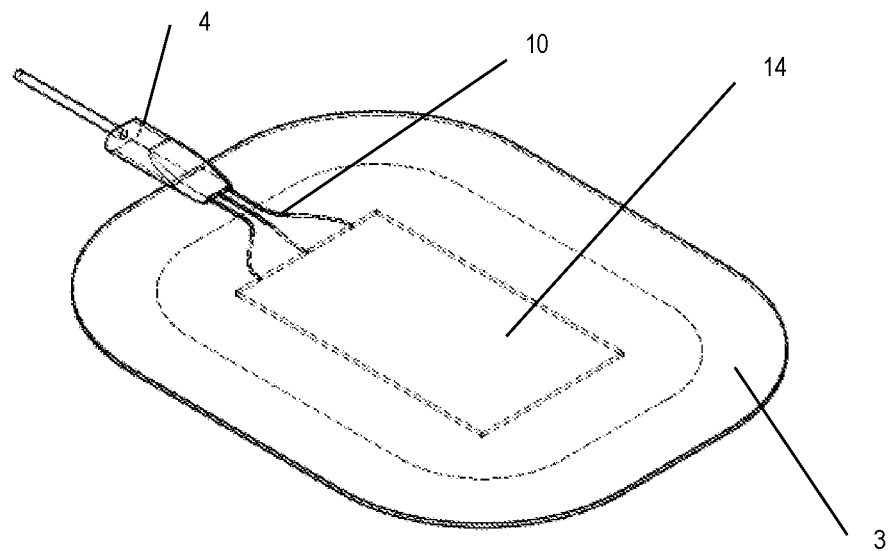
FIG. 10 is a perspective view of another embodiment for light treatment with diffusive light.
Figure 11:
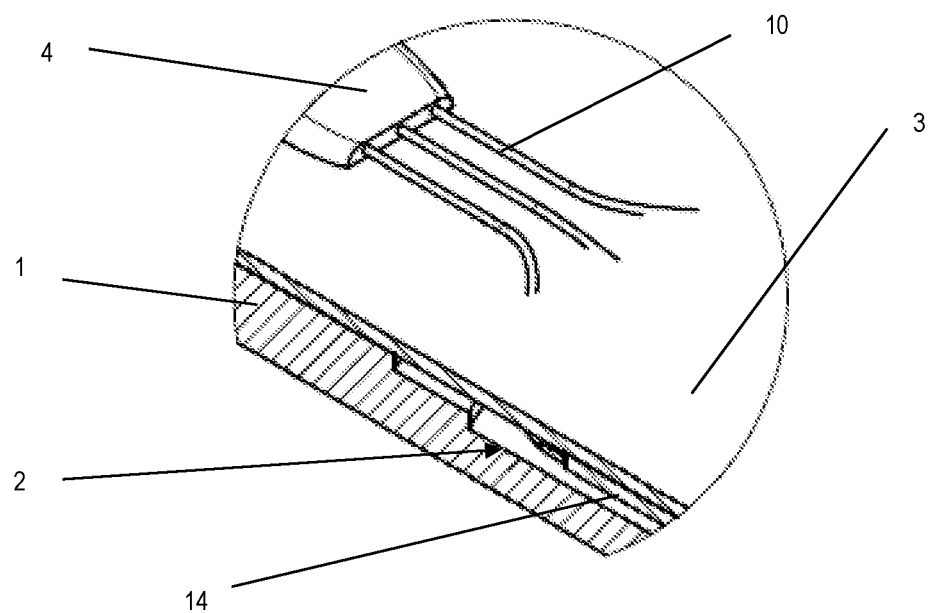
FIG. 11 is a detailed sectional view of the embodiment of FIG. 10.

The light treatment may as well be performed by a diffuse light emitting disk 14, as shown in FIGS. 10 and 11. The diffuse light emitting disk 14 therefore is arranged at the lower surface of wrapping 3, thereby lying just on top of the wound 2.

Furthermore, for a mechanical healing treatment of the wound 2, e.g. by sending ultrasound waves or vibrational energy toward the wound 2, respective elements can be arranged in the wrapping 3. Preferably, an ultrasound transducer, controlled by a controller situated in the apparatus box 5, can be arranged as treatment element 12 in the lower surface of wrapping 3. Alternatively, a vibrational transmitter driven by an electromagnetic arrangement can be arranged in wrapping 3 for transmitting vibrational energy locally into the area of the wound 2.

It is an advantage of the inventive wound treatment dressing that it is composed of a basic apparatus box 5 and a configurable wrapping 3 comprising at least two of several wound healing stimulation means. Thus, an easy but economic production of wound treatment dressings for individual purposes is possible, using only few different parts to be composed together.

A further advantage is the possible combination of different healing stimulation treatments of a wound without the need of changing the wound treatment dressing when changing or altering the healing stimulation treatment. This leads to shorter treatment periods and less danger of infection.

LIST OF REFERENCE SYMBOLS 1 skin
2 wound
3 occlusive wrapping
4 connector
5 external apparatus box
6 connecting pipe
8 cable (for sensor)
9 sensor (pressure)
10 wire
11 junction (of wire)
12 treatment element
13 suction tube
14 light emitting disk (diffuse)

15 optical fiber
16 head of optical fiber

What is claimed is:

1. A multifunctional wound treatment dressing, comprising an occlusive wrapping adapted for placing over a wound on the surface of a skin to define a wound space underneath the wrapping, one side of the wrapping intended to face the wound and comprising a connector to be connected with an external apparatus box, further comprising a combination of at least two different means selected from the group consisting of:
  a negative pressure means comprising a negative-pressure suction tube for applying a negative pressure to the wound space such that the wrapping forms a substantially fluid-tight seal around the wound;
  an electrical stimulation means, comprising at least one electrode arranged at the wrapping and adapted for transmitting electrical energy towards the wound;
  an optical stimulation means, comprising an optical energy conducting and/or emitting element arranged at the wrapping and adapted for transmitting optical energy towards the wound; and
  a mechanical stimulation means, comprising a vibrational energy source arranged at the wrapping and adapted for transmitting vibrational energy towards the wound, wherein the wrapping is rigid or partly rigid.

2. The multifunctional wound treatment dressing according to claim 1, characterized in that the wrapping is rigid.

3. The multifunctional wound treatment dressing according to claim 1, characterized in that the wrapping is customized according to a specific shape of a body part at which the wound is located.

4. The multifunctional wound treatment dressing according to claim 1, characterized in that it further comprises a sensor for determining a state or status of the wound.

5. The multifunctional wound treatment dressing according to claim 4, characterized in that the sensor comprises an optical sensor adapted for illuminating the wound and collecting information regarding the wound scattering parameters.

6. The multifunctional wound treatment dressing according to claim 4, characterized in that the sensor is configured to monitor pH, temperature, tissue closure, infection, biomarkers of healing, enzymes or moisture level.

7. The multifunctional wound treatment dressing according to claim 1, characterized in that it further comprises:
  a wound exudate removing means comprising an exudate-removing suction tube for removing wound exudates from an interior of the wrapping to an exterior of the wrapping, and
  fluid exudate analyzing means for analyzing fluid exudate removed from the wound via the exudate-removing suction tube to identify progress of wound healing and determine one or more analytes indicative of one or more biochemical reactions that occur during wound recovery.

8. The multifunctional wound treatment dressing according to claim 1, characterized in that it further comprises a control unit adapted for adjusting parameters in the wound treatment dressing and/or at the wound site based on data provided by a sensor.

9. The multifunctional wound treatment dressing according to claim 1, characterized in that the electrical stimulation means is adapted for providing pulsed electrical stimulation, wherein the electrical stimulation means is capable of delivering electrical pulses at a pre-selected or controllable pulse rate and intensity, and wherein the electrical stimulation means is adjustable in response to changes in the determined state or status of the wound.

10. The multifunctional wound treatment dressing according to claim 1, characterized in that the optical stimulation means is adapted to provide at least one of an infrared (IR), near-infrared (NIR), and ultraviolet (UV) emission towards the wound.

11. The multifunctional wound treatment dressing according to claim 1, characterized in that the optical stimulation means is adapted for providing pulsed optical stimulation and is capable of delivering optical pulses at a pre-selected or controllable pulse rate and intensity.

12. The multifunctional wound treatment dressing according to claim 1, characterized in that the optical energy conducting and/or emitting element is adapted for providing a selected light across the wound site, wherein the optical energy conducting and/or emitting element comprises a light conducting substrate and at least one emitter mounted to emit light into the substrate.

13. The multifunctional wound treatment dressing according to claim 12, characterized in that the optical energy emitting element comprises a plurality of emitting sources arranged at spaced locations along at least a portion of a periphery of the wound site, or comprises at least one light emitting diode, or comprises at least one optical fiber.

14. The multifunctional wound treatment dressing according to claim 13, characterized in that the optical fiber is split at one end to form a plurality of sub-fibers.

15. The multifunctional wound treatment dressing according to claim 1, characterized in that it comprises the external apparatus box and a connection arrangement, the connection arrangement being adapted to receive one or more optical fibers and/or cables and/or wires and/or suction tubes and being further adapted for providing a connection to at least two different members selected from the group consisting of:
  a pumping means for generating a sub-atmospheric pressure;
  an electrical power source;
  an optical source; and
  a control unit.

16. The multifunctional wound treatment dressing according to claim 15, characterized in that the pumping means comprises a vacuum pump.

17. The multifunctional wound treatment dressing according to claim 15, characterized in that the optical source is an IR, NIR, or UVB source.

18. A method for a therapeutic wound treatment using a multifunctional wound treatment dressing according to claim 1, by forming a substantially fluid-tight seal with the occlusive wrapping around the wound and by combining at least two different members selected from the group consisting of:
  applying a negative pressure around the wound by the wrapping;
  transmitting electrical energy towards the wound from the wrapping;
  transmitting optical energy towards the wound from the wrapping;
  transmitting vibrational energy towards the wound from the wrapping; and
  removing wound exudates to the exterior of the wrapping.

19. A multifunctional wound treatment dressing, comprising an occlusive wrapping adapted for placing over a wound on the surface of a skin to define a wound space underneath the wrapping, one side of the wrapping intended to face the wound and comprising a connector to be connected with an external apparatus box, further comprising a combination of at least two different means selected from the group consisting of:
- a negative pressure means comprising a negative-pressure suction tube for applying a negative pressure to the wound space such that the wrapping forms a substantially fluid-tight seal around the wound;
- an electrical stimulation means, comprising at least one electrode arranged at the wrapping and adapted for transmitting electrical energy towards the wound;
- an optical stimulation means, comprising an optical energy conducting and/or emitting element arranged at the wrapping and adapted for transmitting optical energy towards the wound; and
- a mechanical stimulation means, comprising a vibrational energy source arranged at the wrapping and adapted for transmitting vibrational energy towards the wound; and
- a wound exudate removing means comprising an exudate removing suction tube for removing wound exudates from the wound space, wherein the wrapping is rigid or partly rigid,
wherein the electrical stimulation means is adapted for providing pulsed electrical stimulation, wherein the electrical stimulation means is capable of delivering electrical pulses at a pre-selected or controllable pulse rate and intensity, and wherein the electrical stimulation means is adjustable in response to changes in the determined state or status of the wound, and
wherein the electrical stimulation means comprises an array of electrodes and is adapted for creating at least one composite electrode from at least one of the electrodes in the array, wherein the electrode composition of the at least one composite electrode is adjustable in response to changes in the determined state or status of the wound.

20. A multifunctional wound treatment dressing comprising:
- an occlusive wrapping adapted for placing over a wound on the surface of a skin to define a wound space underneath the wrapping, one side of the wrapping intended to face the wound and comprising a connector to be connected with an external apparatus box, wherein the wrapping is rigid or partly rigid;
- an electrical stimulation means, comprising at least one electrode arranged at the wrapping and adapted for transmitting electrical energy towards the wound, wherein the electrical stimulation means is adapted for creating at least one composite electrode, an electrode composition of the at least one composite electrode being adjustable in response to changes in a determined state or status of the wound; and
- at least one means selected from the group consisting of:
  - a negative pressure means comprising a negative-pressure suction tube for applying a negative pressure to the wound space such that the wrapping forms a substantially fluid-tight seal around the wound;
  - an optical stimulation means, comprising an optical energy conducting and/or emitting element arranged at the wrapping and adapted for transmitting optical energy towards the wound;
  - a mechanical stimulation means, comprising a vibrational energy source arranged at the wrapping and adapted for transmitting vibrational energy towards the wound; and
  - a wound exudate removing means comprising an exudate-removing suction tube for removing wound exudates from the wound space.

\* \* \* \* \*